United States Patent [19]

Augros

[11] 4,338,952
[45] Jul. 13, 1982

[54] DEVICE FOR TAKING SAMPLES OF ENDOMETRIUM

[75] Inventor: Jacques Augros, Villiers le Bel, France

[73] Assignee: Arts et Techniques Nouvelles, Paris, France

[21] Appl. No.: 113,254

[22] Filed: Jan. 18, 1980

[30] Foreign Application Priority Data

Jan. 24, 1979 [FR] France ................................ 79 01832

[51] Int. Cl.³ ............................................ A61B 10/00
[52] U.S. Cl. ..................................... 128/757; 128/751; 128/304; 128/305
[58] Field of Search ............... 128/751, 752, 753, 757, 128/758, 304, 305, 130, 303.14, 304.3

[56] References Cited

U.S. PATENT DOCUMENTS

| | | | |
|---|---|---|---|
| 618,521 | 1/1899 | Palmer | 128/304 |
| 687,112 | 11/1901 | Bowker | 128/304 |
| 928,011 | 7/1909 | Whitlock | 128/304 |
| 1,092,914 | 4/1914 | Jones | 128/304 |
| 3,472,230 | 12/1966 | Fogarty | 128/304 |
| 3,491,747 | 1/1970 | Robinson | 128/757 |
| 3,502,082 | 3/1970 | Chatfield | 128/304 |
| 3,670,732 | 6/1972 | Robinson | 128/304 |
| 3,800,781 | 4/1974 | Zalucki | 128/304 |

OTHER PUBLICATIONS

Gma–Heft, 2/23/78, #A61B-17/38 77 35 281, Richard Wolf (UK Pat. Applic. 2011258A for translation).

Primary Examiner—Kyle L. Howell
Assistant Examiner—Nancy A. B. Swisher
Attorney, Agent, or Firm—James E. Nilles

[57] ABSTRACT

The present invention relates to a device for taking samples of endometrium, or curette, said device comprising a scraper device fixed to the end of a rod which slides in a tube; the scraper device is constituted by two blades subtended by a bow-shaped member, a sphere at the end forming a stop for the return of the device in the tube while two tongues form stop for the slide of the rod when the scraper device emerges.

7 Claims, 1 Drawing Figure

U.S. Patent   Jul. 13, 1982   4,338,952
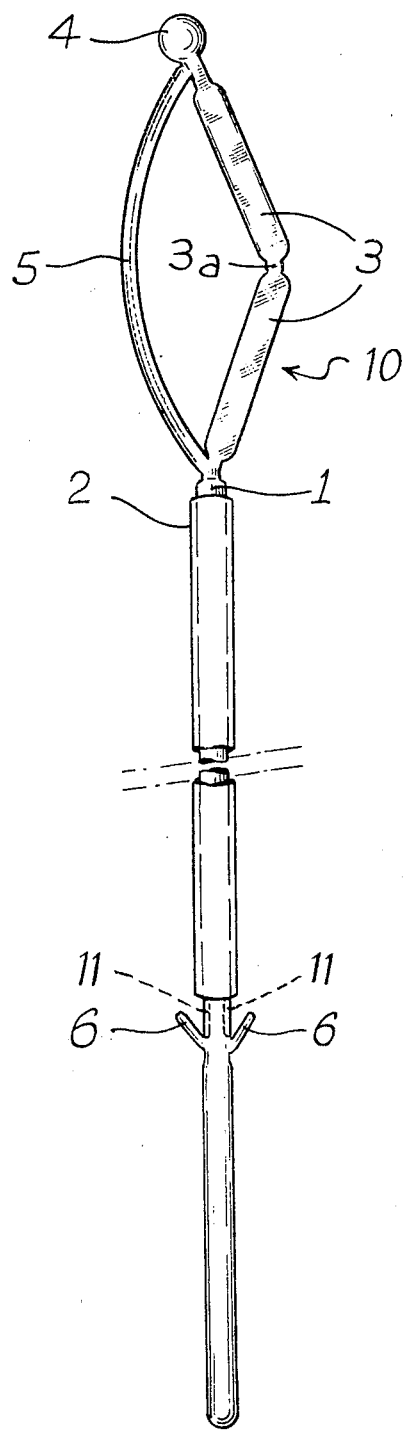

DEVICE FOR TAKING SAMPLES OF ENDOMETRIUM

BACKGROUND OF THE INVENTION

The present invention relates to a device for taking samples of endometrium, or curette, composed of at least one scraper element of elongated form comprising at least one blade, this scraper element being fixed at the end of a rod sliding in a tube inside which said scraper element may be introduced by pulling the rod in the tube.

In this device, the scraper element is reintroduced into the tube, after use, by pulling on the rod, so that the device may be removed from the body without contaminating the sample taken.

In known devices of this type (U.S.Pat. Nos. 3,635,222 and 3,491,747), the scraper element comprises teeth which, when said scraper element is reintroduced into the tube, scrape the wall from which a sample of endometrium is to be taken.

In these known devices, the teeth bend during the sampling operation and consequently they scrape the wall from which the sample must be taken badly, with the result that only a small sample is obtained.

SUMMARY OF THE INVENTION

The device according to the invention remedies this drawback by proposing a device for taking a larger sample without risk of injury to the wall.

This purpose is achieved, according to the invention, in that said scraper element is arched and it is subtended by a bow-shaped member of which the convex side is facing away from the scraper element, whereby, when said scraper element provided with the bow-shaped member is introduced into a cavity of a biological being and the rod is pivoted about its axis, the scraper element undergoes a substantially helical torsion.

The length of the bow-shaped member is advantageously shorter than that of the scraper element.

The scraper element is advantageously constituted by a plurality of blades connected end to end which, under the effect of the bow-shaped member subtending the scraper element, each form an obtuse angle with an adjacent blade.

The adjacent blades are advantageously connected together by a narrow, elastically deformable part.

The end of the scraper element advantageously comprises a sphere whose diameter is greater than that of the tube in order to form stop when this scraper element is returned into the tube.

The end of the rod opposite the scraper element and which is outside the tube, advantageously comprises at least one tongue which forms stop for the slide of the rod in the tube in order to ensure that, when said tongue is in stop position, the scraper element has emerged from the tube, this tongue flattening against the rod when said latter is introduced into the tube.

The scraper element, the bow-shaped member and the rod and, if necessary, the sphere and the stop tongue, are in one piece, cast from plastics material.

The invention will be more readily understood on reading the following description with reference to the accompanying drawings, in which:

The single FIGURE shows a view in elevation of a device according to the invention.

DESCRIPTION OF THE INVENTION

The device for taking samples, or curette, according to the invention is constituted by a rod 1 of suitable length, one of the ends of which termines in a scraper device 10. This rod 1 slides in a tube 2.

The scraper device 10 is constituted by two blades 3 connected by a narrow, elastically deformable part 3a, forming hinge; the blades 3 form an obtuse angle with each other; one of the blades 3 is connected to the rod 2 and the others to a sphere—or ball—4. This sphere 4 and the bottom blade 3 are connected by a bow-shaped member 5 which subtends the arch formed by the blades 3; the convex side of the bow-shaped member 5 faces away from the blades 3; the length of the bow-shaped member 5 is preferably slightly shorter than that of the two blades 3 placed end to end which form the actual scraper element 10.

At the other end of the rod 2, two tongues 6 disposed on each side, allow passage of the tube 2 (for assembly of the device) by folding into a housing 11 provided to this end in the rod 1. These tongues 6 subsequently form stop limiting the slide of the rod 1 in this tube 2.

For using the device, the tube 2 is held and the rod 1 is pulled downwardly, the scraper assembly 3, 4, 5, 10 penetrating in the tube until the sphere 4 stops against the end of the tube 2, this sphere having a larger diameter than that of the tube 2.

It is then easy to introduce the device into the cavity of the biological being without collecting elements foreign to the desired sample, on the way.

When the device is in position, by pushing the rod 1 in the tube 2, the scraper device 3, 4, 5, 10 emerges and takes its initial form, the stops 6 preventing an excessive slide of the rod 1 in the tube 2. By rotating the rod 1 about its longitudinal axis in the tube 2, a movement of rotation is imparted to the scraper device and the blades 3, under the pressure due to the support of the bow-shaped member 5, may thus scrape and take a sample of the mucous membrane to be examined. This combination of support and rotation causes the scraper device to twist, obliging the blades 3 to take a helical position at a certain angle, this enabling a larger sample to be taken, without risk of injury which would cause bleeding rendering the subsequent reading of the sample difficult.

After this rotation, it suffices to return the scraper device into the tube 2 by pulling on the rod 1 until the sphere 4 comes into abutment, the sample taken then being protected from the inevitable contaminations when being removed from the place where it is taken.

The reverse manoeuvre is then made and the sample is spread on a microscope slide for examination.

The device which has just been described may be made by molding in plastics material; the elements 1, 3, 4, 5, 10 are advantageously cast in one piece. By its design, this device enables clean and precise samples to be taken from a large surface and without traumatism during this operation.

Various modifications may, of course, be made by the man skilled in the art to the device which has just been described solely by way of non-limiting example, without departing from the scope of the invention; in particular, the two blades 3 may be replaced by a single arched blade subtended by the bow-shaped member 5.

What is claimed is:

1. In a device for taking samples of endometrium, or curette, comprising a rod, a tube, at least one scraper element of elongated form and comprising at least one blade, said scraper element being fixed at the end of said rod which is slideable in said tube inside which said scraper element may be introduced by pulling said rod in said tube, and a bow-shaped member, said scraper element being arched and subtended by said bow-shaped member of which the convex side is facing away from said scraper element, said scraper element and said bow-shaped member lying in a common plane, the straight-line length of said bow-shaped member being shorter than the straight-line un-arched length of said scraper element so that, when said scraper element provided with said bow-shaped member is introduced into a cavity of a biological being wherein the cavity walls force the bow-shaped member toward said scraper element and said rod is pivoted about its axis, said scraper element undergoes a substantially helical torsion to angle said blade relative to said common plane.

2. The device of claim 1, wherein said scraper element comprises a plurality of blades connected end to end which, under the effect of said bow-shaped member subtending said scraper element, each form an obtuse angle with an adjacent blade.

3. The device of claim 2, wherein the adjacent blades are connected together by a narrow, elastically deformable part.

4. The device of claim 1, wherein said scraper element has an end remote from said rod at which is located a sphere whose diameter is greater than that of said tube in order to form a stop when said scraper element is returned into the tube.

5. The device of claim 1, wherein the end of said rod opposite said scraper element and which is outside said tube, comprises at least one tongue which forms a stop for the sliding of said rod in said tube in order to ensure that, when the tongue is in stop position, said scraper element has emerged from said tube, said tongue flattens against said rod when the latter is introduced into said tube.

6. The device of claim 1, wherein said scraper element, said bow-shaped member and said rod are in one piece, and integrally formed from plastics material.

7. The device of claim 1, wherein said scraper element has an end remote from said rod at which is located a sphere whose diameter is greater than that of said tube in order to form a stop when said scraper element is returned into the tube; wherein the end of said rod opposite said scraper element and which is outside said tube, comprises at least one tongue which forms a stop for the sliding of said rod in said tube in order to ensure that, when the tongue is in stop position, said scraper element has emerged from said tube, said tongue flattens against said rod when the latter is introduced into said tube; and wherein said scraper element, said bow-shaped member, said rod, said sphere and said stop tongue are in one piece, and integrally formed from plastics material.

* * * * *